United States Patent
Al-Dabbagh et al.

(10) Patent No.: US 12,019,059 B2
(45) Date of Patent: Jun. 25, 2024

(54) DETECTING EQUIPMENT DEFECTS USING LUBRICANT ANALYSIS

(71) Applicant: SAUDI ARABIAN OIL COMPANY, Dhahran (SA)

(72) Inventors: Fairouz Al-Dabbagh, Al Khobar (SA); Abdulrahman Al-Omair, Al Khobar (SA); Ahmed Al-Zahrani, Al Khobar (SA); Hasanur Jamal Molla, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 868 days.

(21) Appl. No.: 17/072,450

(22) Filed: Oct. 16, 2020

(65) Prior Publication Data

US 2022/0120727 A1     Apr. 21, 2022

(51) Int. Cl.
*G01N 33/28*     (2006.01)
*G01M 13/00*     (2019.01)
(Continued)

(52) U.S. Cl.
CPC ........ *G01N 33/2888* (2013.01); *G01M 13/00* (2013.01); *G05B 23/0218* (2013.01);
(Continued)

(58) Field of Classification Search
CPC ... G01N 33/2888; G06F 16/285; G06F 18/24; G06F 11/3065; G06N 20/00; G01M 13/00; G05B 23/0218
See application file for complete search history.

(56) References Cited

U.S. PATENT DOCUMENTS 6,598,464 B1    7/2003   Rossi
7,581,434 B1 *   9/2009   Discenzo ........... G01N 33/2888
                                                  73/53.01
(Continued)

FOREIGN PATENT DOCUMENTS

CN     100567950 C    12/2009
CN     102606561 B     9/2015
(Continued)

OTHER PUBLICATIONS

Wang Q, et al. A Novel Ensemble Method for Imbalanced Data Learning: Bagging of Extrapolation—SMOTE SVM. Comput Intell Neurosci. 2017; Epub Jan. 30, 2017 (Year: 2017).*
(Continued)

*Primary Examiner* — Mohamed Charioui
*Assistant Examiner* — Lyudmila Zaykova-Feldman
(74) *Attorney, Agent, or Firm* — Osha Bergman Watanabe & Burton LLP

(57) ABSTRACT

A system for automatic detection of a defect in equipment may include a binary classification model trained to classify laboratory analysis results of an oil sample according to a gradient boosting algorithm, and to output a classification indicator of "good" or "defective" for the laboratory analysis results of the oil sample. The system may include a first multiclass classification model trained to classify the laboratory analysis results according to the gradient boosting algorithm if the laboratory analysis results are classified as "defective," and to output a predicted defect type for the defect in equipment. The system may include a second multiclass classification model trained to classify the laboratory analysis results according to the gradient boosting algorithm and the predicted defect type, and to output a predicted corrective action pertaining to the equipment
(Continued)

based on the predicted defect type for the defect in equipment.

18 Claims, 7 Drawing Sheets

(51) Int. Cl.
| | | |
|---|---|---|
| G05B 23/02 | (2006.01) | |
| G06F 11/30 | (2006.01) | |
| G06F 16/28 | (2019.01) | |
| G06F 18/24 | (2023.01) | |
| G06N 20/00 | (2019.01) | |

(52) U.S. Cl.
CPC ........ *G06F 11/3065* (2013.01); *G06F 16/285* (2019.01); *G06F 18/24* (2023.01); *G06N 20/00* (2019.01)

(56) References Cited

U.S. PATENT DOCUMENTS

| | | | |
|---|---|---|---|
| 8,155,891 B2 | 4/2012 | Kong et al. | |
| 9,824,060 B2 | 11/2017 | Yacout et al. | |
| 2007/0032964 A1* | 2/2007 | Kaldor | G01N 33/30 |
| | | | 702/189 |
| 2008/0086437 A1 | 4/2008 | Yuan et al. | |
| 2013/0132001 A1* | 5/2013 | Yacout | G01D 3/10 |
| | | | 702/35 |
| 2014/0309959 A1* | 10/2014 | Shen | G01N 33/241 |
| | | | 702/100 |
| 2019/0095792 A1* | 3/2019 | Kashinath | G06N 20/20 |
| 2019/0156600 A1 | 5/2019 | Potyrailo et al. | |
| 2019/0166606 A1* | 5/2019 | Kalderen | H04W 24/02 |
| 2020/0027028 A1 | 1/2020 | Shi et al. | |
| 2020/0033317 A1* | 1/2020 | Patel | C10G 75/04 |
| 2020/0067789 A1 | 2/2020 | Khuti et al. | |
| 2020/0103894 A1 | 4/2020 | Cella et al. | |
| 2020/0292450 A1* | 9/2020 | Kojima | G01N 21/78 |
| 2021/0142177 A1* | 5/2021 | Mallya | G06N 3/084 |
| 2022/0222931 A1* | 7/2022 | Goyal | G06V 10/7747 |

FOREIGN PATENT DOCUMENTS

| | | |
|---|---|---|
| HU | 183572 B | 5/1984 |
| WO | 2005086760 A2 | 9/2005 |
| WO | 2018/187898 A1 | 10/2018 |
| WO | WO-2019041629 A1 * | 3/2019 |
| WO | 2020/154461 A1 | 7/2020 |

OTHER PUBLICATIONS

H.-Y. Wang, "Combination approach of SMOTE and biased-SVM for imbalanced datasets," 2008 IEEE International Joint Conference on Neural Networks (IEEE World Congress on Computational Intelligence), Hong Kong, China, 2008, pp. 228-231 (Year: 2008).*
Zhang, WO2019041629A1, Classification method for high-dimensional unbalanced data based on SVM technical field, downloaded from Espacenet on Aug. 12, 2023 (Year: 2019).*
International Search Report and Written Opinion of the International Searching Authority issued in corresponding International Application No. PCT/US2021/055231, dated Jan. 27, 2022 (15 pages).

* cited by examiner

DETECTING EQUIPMENT DEFECTS USING LUBRICANT ANALYSIS

BACKGROUND

Generally, as part of industrial operations, engineers or technicians monitor the condition of equipment utilized in the industrial operations in order to prevent equipment failure and resulting interruptions. A current approach to monitoring the condition of equipment is to regularly collect samples of oil (hereinafter also "lubricant") utilized in the operation of the equipment, send the oil samples to a laboratory for analysis, and receive analysis results from the laboratory. The analysis results may include assessments, by industry experts, regarding the condition of the analyzed oil samples. The experts rely in their analysis on industrial standard thresholds and domain expertise to identify the quality of the analyzed oil. Based on the expert analysis, the engineers or technicians recommend corrective actions for the efficient maintenance of the equipment. Examples of corrective actions are changing the oil utilized in the equipment, making a modification in the operation of the equipment, changing a piece of the equipment, or replacing the equipment.

The reliance on an individual engineer's expertise to identify the defect in equipment and propose corrective action may sometimes be insufficient to accurately and efficiently diagnose and correct an equipment defect. In addition, different engineers' approaches to solving the same problem may lead to inconsistent operation of the equipment, which in turn may lead to the exacerbation of the equipment defect.

Accordingly, a need exists for a system to automatically detect defects in equipment and to automatically identify and implement corrective actions based on the results of oil sample analysis and historical expert decisions.

SUMMARY

This summary is provided to introduce concepts that are further described below in the detailed description. This summary is not intended to identify key or essential features of the claimed subject matter, nor is it intended to be used as an aid in limiting the scope of the claimed subject matter.

Embodiments disclosed herein relate to systems and methods for automatic detection and correction of a defect in equipment based on applying machine learning techniques to lubricant analysis.

In general, in one aspect, embodiments disclosed herein relate to a system for automatic detection of a defect in equipment. The system includes one or more hardware processors. The system includes an access module configured to access laboratory analysis results of an oil sample taken from the equipment. The system includes a binary classification model. The binary classification model is trained to classify the laboratory analysis results of the oil sample according to a gradient boosting algorithm. The binary classification model is trained to output a classification indicator of "good" or "defective" for the laboratory analysis results of the oil sample. The system includes a first multiclass classification model. The first multiclass classification model is trained to classify the laboratory analysis results of the oil sample according to the gradient boosting algorithm if the laboratory analysis results are classified as "defective." The first multiclass classification model is trained to output a predicted defect type for the defect in equipment. The system includes a second multiclass classification model. The second multiclass classification model is trained to classify the laboratory analysis results of the oil sample according to the gradient boosting algorithm and the predicted defect type. The second multiclass classification model is trained to output a predicted corrective action pertaining to the equipment based on the predicted defect type for the defect in equipment.

In general, in one aspect, embodiments disclosed herein relate to a method for automatic detection of a defect in equipment. The method includes accessing, by an access module, laboratory analysis results of an oil sample taken from the equipment. The method includes classifying, by one or more hardware processors using a trained binary classification model, the laboratory analysis results of the oil sample according to a gradient boosting algorithm. The method includes outputting, by the one or more hardware processors using the trained binary classification model, a classification indicator of "good" or "defective" for the laboratory analysis results of the oil sample. The method includes classifying, by the one or more hardware processors using a trained first multiclass classification model, the laboratory analysis results of the oil sample according to the gradient boosting algorithm if the laboratory analysis results are classified as "defective." The method includes outputting, by the one or more hardware processors using the trained first multiclass classification model, a predicted defect type for the defect in equipment. The method includes classifying, by the one or more hardware processors using a trained second multiclass classification model, the laboratory analysis results of the oil sample according to the gradient boosting algorithm and the predicted defect type. The method includes outputting, by the one or more hardware processors using the trained second multiclass classification model, a predicted corrective action pertaining to the equipment based on the predicted defect type for the defect in equipment.

In general, in one aspect, embodiments disclosed herein relate to a method for training a plurality of classification models to automatically detect a defect in equipment. The method includes accessing laboratory analysis results of a plurality of oil samples in a training dataset. The method includes training, by one or more hardware processors, a binary classification model to classify the laboratory analysis results of oil samples in the training dataset according to a gradient boosting algorithm, and to output a classification of "good" or "defective" for the laboratory analysis results of the oil samples in the training dataset. The method includes training, by the one or more hardware processors, the first multiclass classification model to classify the laboratory analysis results of the oil samples in the training dataset according to the gradient boosting algorithm if the laboratory analysis results are classified as "defective," and to output the predicted defect type for the defect in equipment. The method includes training, by the one or more hardware processors, a second multiclass classification model to classify the laboratory analysis results of the oil samples in the training dataset according to the gradient boosting algorithm and the predicted defect type, and to output the predicted corrective action pertaining to the equipment based on the predicted defect type for the defect in equipment.

Other aspects and advantages of the claimed subject matter will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

Figure 1:
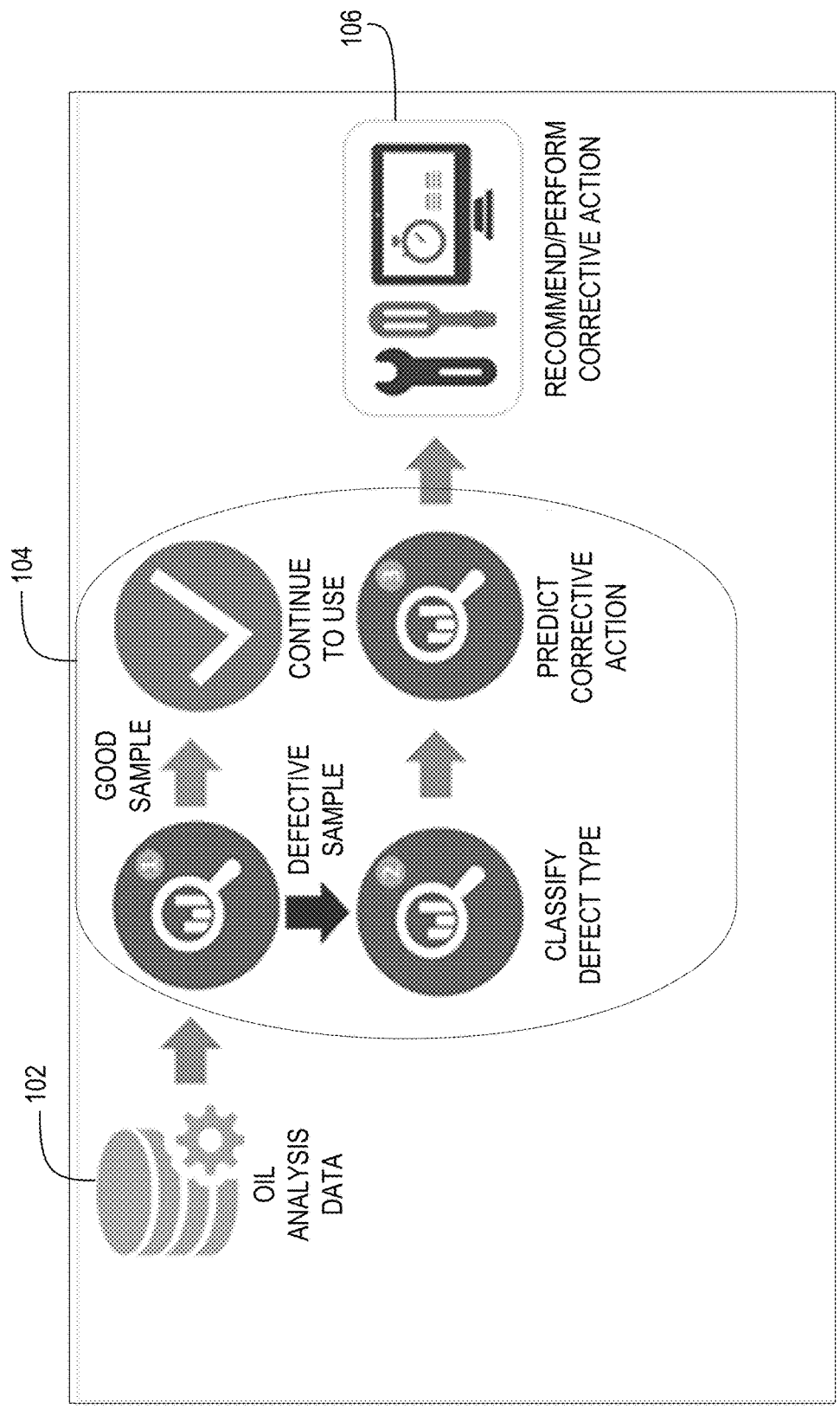
FIG. 1 is a flow diagram that illustrates a diagnostic and correction system, according to one or more example embodiments.

Example systems and methods for automatic detection and correction of a defect in equipment based on applying machine learning techniques to lubricant analysis are described. Unless explicitly stated otherwise, components and functions are optional and may be combined or subdivided. Similarly, operations may be combined or subdivided, and their sequence may vary.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, or third) may be used as an adjective for an element (that is, any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

Traditionally, equipment maintenance in the context of industrial operations includes laboratory testing of lubricant samples taken from items of equipment and interpretation of the laboratory results by industry experts. The industry experts also recommend corrective actions based on the results of the analysis.

In a traditional maintenance system, test slates are designed specifically for various types of lubricant oil (hereinafter also "lube oil" or "oil"). A test slate may test an oil sample for a number of different parameters (e.g., aspects, attributes, or characteristics) associated with oil samples using routine and non-routine tests. Examples of oil tests are elemental analysis, viscosity tests, water screening, acid number tests, particle density analysis, and analytical ferrography. A parameter may be a chemical component or composition present in the oil sample, or a physical characteristic of the oil sample. Examples of parameters are water, particles, wear metals, fuels, silicon, coolant, viscosity level, additive metals, and flash point level. In some instances, each parameter considered under specific test slates has a particular condemnation limit (e.g., a threshold value) specified based on international standards, industry best practices, or equipment manufacturer's recommendations. The traditional system screens the oil samples for the parameters using a test slate corresponding to particular oil samples, and identifies the parameters for which the test results are outside (e.g., below or above) the set condemnation limit.

The traditional maintenance system recognizes the failure mode for specific oil samples based on the test results which fall outside the set condemnation limit, and selects a recommendation specific to the recognized failure mode based on observation and application. However, there is a need for a diagnostic and correction system that improves upon the traditional approach of identifying equipment defects based on applying machine learning to lubricant analysis results.

In some example embodiments, the diagnostic and correction system trains one or more machine learning (hereinafter also "ML") models to classify oil samples as good or defective using the data derived from the analysis of various oil samples and historical expert decision data made based on the sample analysis. The one or more ML models are also trained to identify the type of defect associated with the defective oil sample, and to identify a suitable corrective action for the defect. The training of the one or more ML models facilitates the automatic recognition of patterns in the sample analysis data associated with various types of equipment defects, the identifying of equipment defects using the recognized patterns, and the automatic recommendation or implementation of corrective action. When the pattern of the defect is recognized and predicted, the appropriate corrective action is also predicted and recommended based on historical data that was analyzed by experts. In some instances, the automatic recognition of patterns and the automatic recommendation or implementation of corrective action facilitates quick attendance to issues that may result in operational cost savings.

In some example embodiments, determining the defect and the corrective action for the defect is performed in three phases. At least three types of ML models are trained for the three phases. A supervised ML algorithm (e.g., a gradient boosted decision tree or a gradient boosting algorithm) is applied to laboratory analysis data of oil samples during the three phases. An example of such a supervised ML algorithm is the Extreme Gradient Boost algorithm (XGBoost).

During the first phase, a first, binary ML model (or binary ML classifier) is built (or trained) to classify input laboratory analysis results (also "lab analysis data," "lab results," or "lab records") of a plurality of oil samples as good or defective. In this phase, there are two classes available for the classification of the lab results by the first, binary ML model: good and defective (or bad). For example, good may be assigned the binary value of 0, while bad may be assigned a binary value of 1, or vice versa.

In some example embodiments, when an analyst tests an oil sample, the oil sample is marked as a good sample or a defective sample. A dataset may be generated from the records of a plurality (e.g., tens of thousands) of oil samples for the categorization into the two classes during the first phase of prediction. For each oil sample, the dataset includes a plurality of features. The features correspond to attributes (e.g., parameters or characteristics) identified during the testing of the oil samples. Examples of features are "Aluminum," "Antimony," "Appear," "Barium," "Boron," "Base Sediment & Water," "Cadmium," "Calcium," "Chromium," "Color," "Copper," "FERL," "FERS," "Filter," "Flash Point," "Foam," "Fuel Dilution," "Iron," "Lead," "Magnesium," "Moisture," "Molybdenum," "Nickel," "pH," "Phosphorous," "Rotating Pressure Vessel Oxidation," "Silicon," "Silver," "Sodium," "Solids," "Total Acid Number," "Total Base Number," "Tin," "Titanium," "Viscosity at 100 degrees Celsius (C)," "Viscosity at 40 degrees C.," "Water," "Zinc," "Oil Type," "Oil Sump Capacity," and "Equipment Type." FERS indicates the direct ferrography test result for smaller particles. FERL indicates the direct ferrography test result for large particles. The features are used as predictor values (also "predictors"), while the target value (also "target") is one of the binary values of "0" for good or "1" for defective. The predictor variables are used to predict (e.g., determine) the target variable. In some instances, fewer features may be selected to improve the model.

In some example embodiments, the binary classifier using the XGBoost algorithm is trained on a first percentage (e.g., 80%) of the data, after being oversampled using Synthetic Minority Oversampling Technique (SMOTE) using a support vector machine (SVM) algorithm to detect the sample used for generating new synthetic samples in order to balance the two classes with respect to the data distribution. A second percentage (e.g., 20%) of the oversampled data is used to test the prediction performance of the binary classifier.

During the second phase, a second, multiclass ML model (or a multiclass classifier) is trained to further classify the lab results of the oil samples classified as defective during the first phase. In the second phase, the defective oil samples are classified according to defect type. For each defective oil sample, the dataset includes the all or a subset of the plurality of features mentioned above with respect to the first model. In the second phase, there are four classes available for the classification of the defective oil samples by the second ML model: contamination, oil mixing, dissolved gasses, and degradation.

In some example embodiments, to train the second, multiclass ML model, a subset of the dataset is used. The subset of the dataset comprises only records of defective oil samples. The list of features is used as predictors, while the target is the defect type. The multiclass classifier using the XGBoost algorithm is trained on a first percentage (e.g., 80%) of the data, after being oversampled using SMOTE-SVM to balance the four classes with respect to the data distribution. A second percentage (e.g., 20%) of the oversampled data is used to test the prediction performance of the second, multiclass ML model.

During the third phase, a third, multiclass ML model (or a multiclass classifier) is trained to predict corrective actions for each defect type. In the third phase, the input data includes the defective oil samples of each type of defect. In some instances, a model is trained for each defect type. Each defect type may have a different number or set of corrective actions. The number of corrective actions may vary from one defect type to another. For example, one defect type may have 5 corrective actions, while another may have 7 corrective actions.

In some example embodiments, a particular defect dataset is created, for each defect type, from the records identifying the defective oil samples. For each defect dataset, a particular multiclass ML model is trained. The list of features is used as predictors, while the target is the corrective action for the particular defect type. The multiclass classifier using the XGBoost algorithm is trained on a first percentage (e.g., 80%) of the data, after being oversampled using SMOTE-SVM to balance the classes with respect to the data distribution. A second percentage (e.g., 20%) of the oversampled data is used to test the prediction performance of each of the particular multiclass ML models.

An advantage provided by the diagnostic and correction system is the ability to accurately identify equipment defects and provide timely corrective actions based on applying machine learning techniques to records describing laboratory results of oil samples. In addition to improving accuracy and timeliness, the diagnostic and correction system enhances data processing efficiency.

FIG. 1 is a flow diagram that illustrates a diagnostic and correction system 104, according to one or more example embodiments. The diagnostic and correction system 104 accesses oil analysis data 102 from a data repository, and uses the oil analysis data 102 as input for one or more machine learning models that identify and classify equipment defects and identify corresponding corrective actions based on the identified equipment defects. For example, the oil analysis data 102 may include laboratory records (hereinafter also "lab records," "data records," or "records") for an oil sample that has been tested to identify various characteristics associated with the oil sample. The oil sample is classified, using a first ML model, as a normal oil sample or a defective oil sample. If the oil sample is classified as a defective oil sample, the defective oil sample is then classified, using a second ML model, according to defect type. Then, a third ML model predicts a correction action based on the defect type of the defective oil sample. Thus, each oil sample may go through one or multiple ML models, depending on whether the sample is identified as normal, or whether the sample is classified as a defect. Training of the ML models is done on historical datasets.

In some example embodiments, the diagnostic and correction system 104 trains a plurality of ML models in three phases. During the training of the plurality of ML models, the diagnostic and correction system 104 may use records of oil samples selected specifically for the training of the ML models (hereinafter also "oil samples in the training dataset").

As shown in FIG. 1, during the first phase, the diagnostic and correction system 104 trains a first ML model to classify oil samples in a training dataset as "good" or "defective." The lab records of the oil samples in the training dataset and associated labels (e.g., "good" or "defective") assigned by experts based on the quality of the oil samples are utilized as input for training the first ML model.

During the second phase, for the oil samples which are defective, the diagnostic and correction system 104 may train a second ML model to classify the defect as one of a plurality of defect types. Upon determining the type of defect, the diagnostic and correction system 104 proceeds to phase three of training, during which the diagnostic and correction system 104 trains a particular ML model corresponding to each defect type in order to predict an appropriate corrective action for the defect.

The diagnostic and correction system 104 is configured to generate a recommendation 106 or perform the corrective action with respect to the equipment associated with the oil sample. The diagnostic and correction system 104 may include a computer system that is similar to the computer systems 700 and 714 described with regard to FIGS. 7A and 7B, respectively, and the accompanying descriptions.

Figure 2:
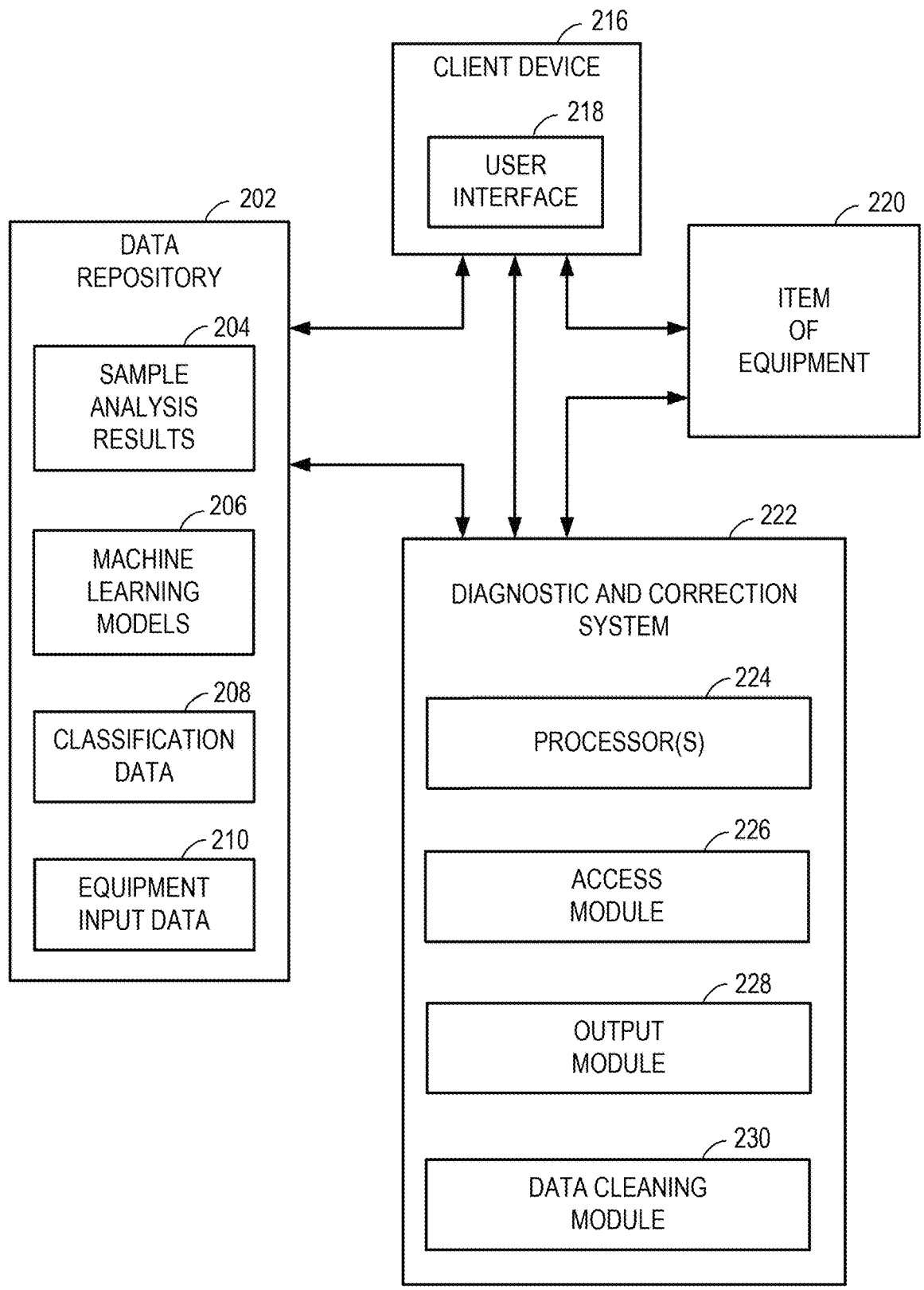
FIG. 2 is a block diagram that illustrates the diagnostic and correction system, according to one or more example embodiments.

FIG. 2 is a block diagram that illustrates the diagnostic and correction system, and the other parts of a system that interact with the diagnostic and correction system, according to one or more example embodiments. The diagnostic and correction system 222 is shown as including one or more hardware processors 224, an access module 226, an output module 228, and a data cleaning module 230. The components of the diagnostic and correction system 222 are operatively connected and are configured to communicate with each other (e.g., via a bus, shared memory, a switch, wirelessly, etc.). In some example embodiments, a plurality of hardware processor(s) 224 are distributed across multiple machines or devices.

As shown in FIG. 2, the diagnostic and correction system 222 is configured to communicate with a data repository 202 to access and store various types of data. The data repository 202 stores sample analysis results 204, machine learning models 206, classification data 208, and equipment input data 210. The data repository may be any type of suitable storage, such as persistent storage, non-persistent storage, etc. Further, the data repository may be configured to store data in any suitable type of data structure, such as arrays, tables, lists, etc.

The access module 226 of the diagnostic and correction system 222 accesses (e.g., receives or obtains) data, such as the sample analysis results 204, from the data repository 202. The sample analysis results 204 may include records associated with various tests performed on oil samples, for example, laboratory analysis results of a plurality of oil samples in the training dataset. The lab analysis records of the oil samples in the training dataset are used to train ML models. The sample analyses results 204 may also include laboratory analysis results of an oil sample (e.g., a field oil sample) taken from the equipment. The lab results of the oil sample are analyzed using the trained ML models to detect the defect of the equipment from which the oil sample was taken.

The sample analysis results 204 include data descriptive of various parameters of the oil samples. The parameters may include characteristics (e.g., viscosity) of oil samples, or components (e.g., silicon, iron, etc.) found in the oil samples during the oil tests.

The sample analysis results 204 may be used to train the ML models 206 (e.g., a binary classification model, a first multiclass classification model, or a second multiclass classification model) to identify equipment defects and generate recommendations for corrective actions associated with the equipment defects. The ML models are trained on the dataset with the corrective action as a target. The models then recognize the pattern and classifies the oil analysis data to the appropriate corrective action. In contrast with the lab records of an oil sample in the training dataset that are used to train a ML model, the lab records of a test oil sample (hereinafter also "field oil sample" or "oil sample") are used by the trained ML model(s) to identify a defect in equipment.

The classification data 208 may be generated by the ML models 206 during the training of the ML models 206 and during the utilization of the trained ML models. Examples of classification data 208 are records indicating that some oil samples are labeled as "defective," records indicating types of defects, and records indicating predicted corrective actions for various defects.

In some example embodiments, the one or more hardware processor(s) 224 train the ML models 206 using the sample analysis results 204. For example, one of the hardware processor(s) 224 (hereinafter "the hardware processor") trains a binary classification model to classify the laboratory analysis results of oil samples in the training dataset according to a gradient boosting algorithm, and to output a classification of "good" or "defective" for the laboratory analysis results of the oil samples in the training dataset. The hardware processor trains the first multiclass classification model to classify the laboratory analysis results of the oil samples in the training dataset according to the gradient boosting algorithm if the laboratory analysis results are classified as "defective," and to output the predicted defect type for the defect in equipment. The hardware processor trains a second multiclass classification model to classify the laboratory analysis results of the oil samples in the training dataset according to the gradient boosting algorithm and the predicted defect type, and to output the predicted corrective action pertaining to the equipment based on the predicted defect type for the defect in equipment.

In some example embodiments, the one or more hardware processor(s) 224 receive a request to identify a defect and propose a corrective action for the defect based on analysis results associated with a particular oil sample (e.g., a field oil sample). Using one or more of the trained ML models 206, the one or more hardware processor(s) 224 identify the defect in an item of equipment 220 associated with the particular oil sample based on classifying the particular oil sample as defective, and identify an appropriate corrective action based on the identified defect. The item of equipment 220 may be certain machinery or a moving part included in the machinery. Examples of the item of equipment 220 are an internal combustion engine, a pump, a gearbox, pipe connections, derrick components (e.g., a crown, a travelling block, top drive, or rough neck), drawworks, and wire ropes. The oil sample may be taken from the lubricant utilized to separate the moving parts in a system by forming a physical barrier between the moving parts. The separation created by the lubricant may reduce friction, wear, surface fatigue, heat generation, operating noise, and vibrations in the system.

Returning to FIG. 2, the hardware processor, using the access module 226, accesses laboratory analysis results of an oil sample taken from the equipment. The hardware processor, using a trained binary classification model, classifies the laboratory analysis results of the oil sample according to a gradient boosting algorithm, and outputs a classification indicator of "good" or "defective" for the laboratory analysis results of the oil sample. The hardware processor, using a trained first multiclass classification model, classifies the laboratory analysis results of the oil sample according to the gradient boosting algorithm if the laboratory analysis results are classified as "defective," and outputs a predicted defect type for the defect in equipment. The hardware processor, using a trained second multiclass classification model, classifies the laboratory analysis results of the oil sample according to the gradient boosting algorithm and the predicted defect type, and outputs a predicted corrective action pertaining to the equipment based on the predicted defect type for the defect in equipment.

The output module 228 may generate a workorder based on the predicted corrective action. The output module 228 may also cause display of the workorder in a user interface 218 of a client device 216.

In some example embodiments, the one or more hardware processor(s) 224 automatically cause the performance of the corrective action. For example, the one or more hardware processor(s) 224 generate the equipment input data 210, and transmit an instruction including a reference to the equipment input data 210 to the item of equipment 220. The equipment input data 210 may be an input value utilized to modify (e.g., cause an adjustment to or cause an improvement in) the operation of the item of equipment 220 in a particular way. The execution of the instruction including the reference to the equipment input data 210, by the item of equipment 220, may result in the elimination or the minimization of the identified defect.

The diagnostic and correction system 222 is also configured to communicate with the client device 216 that includes the user interface 218. The client device 216 may include a computing device that includes at least a display and communication capabilities to communicate with the diagnostic and correction system 222, the data repository 202, and the item of equipment 220 via an electronic network. The client device may comprise, but is not limited to, a computer, a work station, a desktop, a laptop, a tablet, a smart phone, a hand-held device, an Internet appliance, a wearable device, a smart phone, a cellular (or mobile) phone, a multi-processor system, a mini-computer, etc. The user interface 218 may be a graphical user interface (GUI) or a command line interface. The user interface 218 may display data retrieved, accessed, or received from the data repository 202, the diagnostic and correction system 222, and the item of equipment 220 on a display device, such as a computer monitor or a touchscreen on the client device 216. Furthermore, the user interface 218 may present data directly to the user, for example, data presented as actual data values through text, or rendered by the client device 216 into a visual representation of the data, such as through visualizing a data model.

In some example embodiments, the diagnostic and correction system 222 generates a communication that references the identified defect and provides a recommendation of a corrective action with respect to the identified defect. The diagnostic and correction system 222 transmits the communication to the client device 216 and causes display of the communication in the user interface 218 of the client device 216.

In some example embodiments, a user of the client device 216 accesses the diagnostic and correction system 222 via the user interface 218. The user may, for example, make configuration changes to the one or more modules included in the diagnostic and correction system 222. The client device 216 is also configured to communicate with the data repository 202 to access and store data. In addition, the client device 216 is also configured to communicate with the item of equipment 220.

Figure 3:
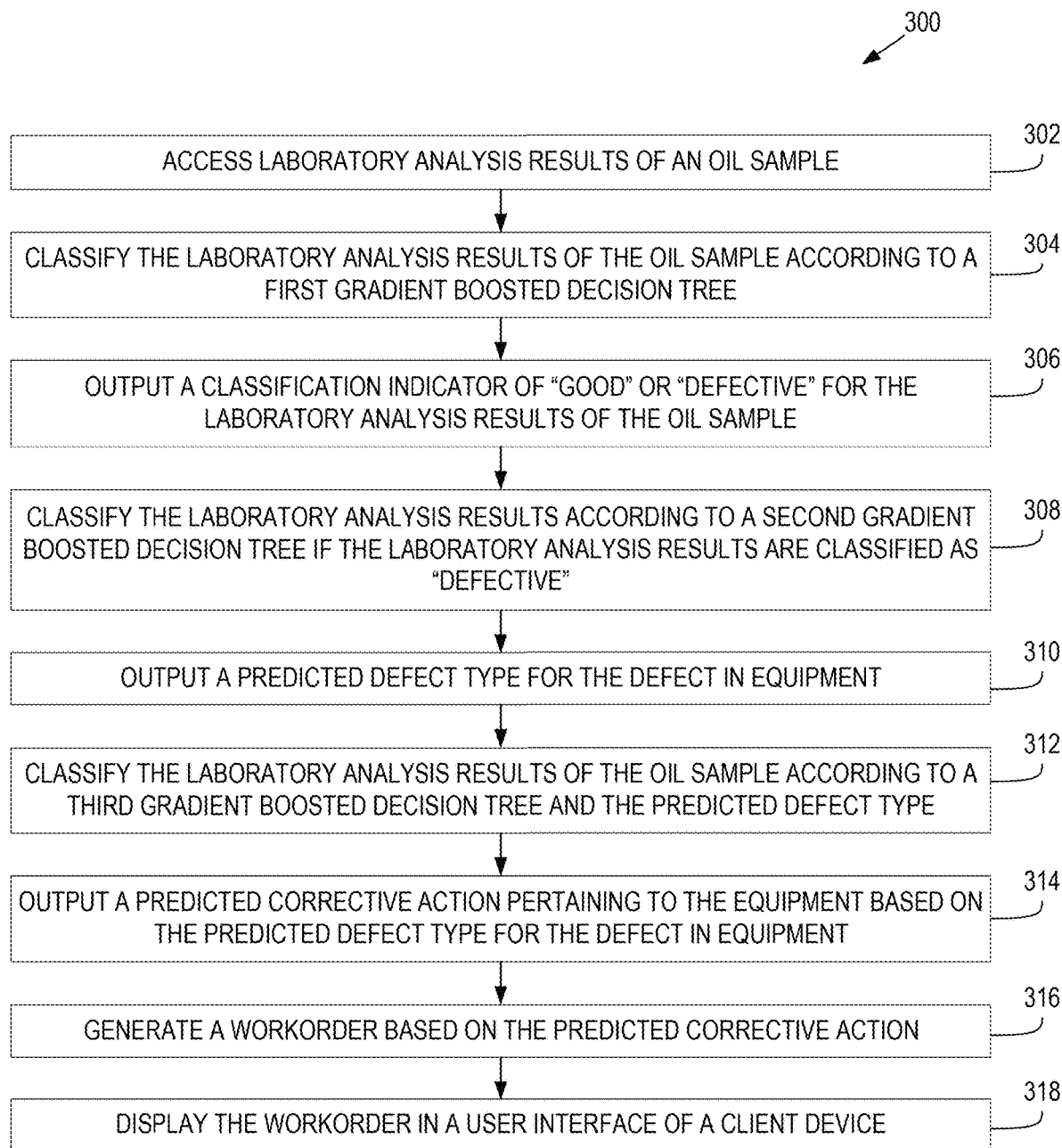
FIGS. 3 and 4 are flowcharts illustrating operations of the diagnostic and correction system in performing a method for automatic detection and correction of a defect in equipment, according to one or more example embodiments.
Figure 4:
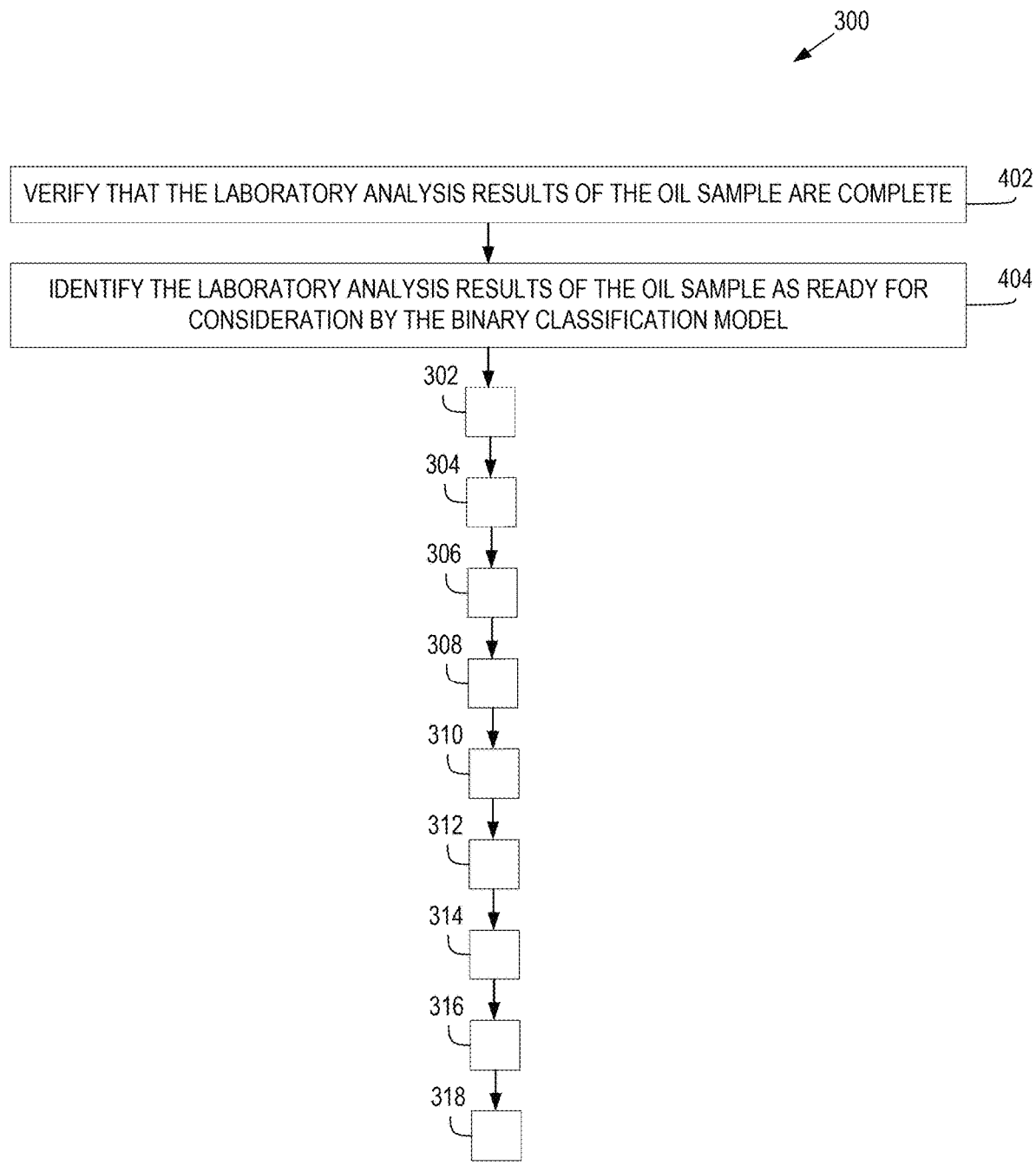

FIGS. 3 and 4 are flowcharts that illustrates operations of the diagnostic and correction system in performing a method 300 for automatic detection of a defect in equipment, according to one or more example embodiments. Operations of the method 300 may be performed using the components described above with respect to FIG. 2. One or more blocks in FIGS. 3 and 4 may be performed by a computing system such as that shown and described below in FIGS. 7A and 7B. While the various blocks in FIGS. 3 and 4 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

At step 302, the access module 226 accesses laboratory analysis results of an oil sample (e.g., a field oil sample) from a data repository (e.g., the data repository 202). The oil sample is collected from the equipment. The equipment may or may not exhibit signs of malfunction. A laboratory performs laboratory analysis of the oil sample associated with the equipment, and generates the laboratory analysis results. The results of the analysis include data descriptive of one or more parameters of the plurality of oil samples. The one or more parameters may describe characteristics (e.g., viscosity or color) of the oil sample, or may indicate the presence of contaminants (e.g., metals, silicon, etc.) in the oil sample.

In some example embodiments, the data cleaning module 230 verifies that the laboratory analysis results of the oil sample are complete and closed. To be a complete and closed record that may be included in a dataset, a record should be labeled and include required features. This allows the ML models to make classification decisions based on adequate information. The data cleaning module 230 identifies (e.g., marks, tags, or places in a container) the laboratory analysis results of the oil sample as ready for consideration by a trained binary classification model.

At step 304, the one or more hardware processors 224 (e.g., a first processor of a first machine) classify, using the trained binary classification model, the laboratory analysis results of the oil sample according to a gradient boosting algorithm. An example of such a gradient boosting algorithm is XGBoost. XGBoost is an optimized distributed gradient boosting library designed to be highly efficient, flexible, and portable. It implements machine learning algorithms under the Gradient Boosting framework. XGBoost provides parallel tree boosting (also known as Gradient Boost Decision Tree (GBDT) or Gradient Boosting Machine (GBM)) that solves many data science problems in a fast and accurate way. The same code runs on major distributed environment (e.g., Hadoop, Sun Grid Engine (SGE), and Message Passing Interface (MPI)) and can solve problems beyond billions of examples.

At step 306, the one or more hardware processors 224 output, using the trained binary classification model, a classification indicator of "good" or "defective" for the laboratory analysis results of the oil sample. If the oil sample is classified as "good," the output module 228 may, in some instances, generate and transmit a communication to the client device 216 that the equipment associated with the oil sample may continue to be used. If an oil sample is classified as "defective," the one or more hardware processors 224 proceed to step 308.

Those skilled in the art will appreciate that "good" and "defective" may be substituted by any appropriate classification identifier that describes the condition of the lab analysis results, and that the scope of this disclosure is not limited to use of "good" and "defective" as classifications.

At step 308, the one or more hardware processors 224 classify, using a trained first multiclass classification model, the laboratory analysis results of the oil sample according to the gradient boosting algorithm if the laboratory analysis results are classified as "defective." At step 310, the one or more hardware processors 224 output, using the trained first multiclass classification model, a predicted defect type for the defect in equipment.

In some example embodiments, the defect type includes at least one of contamination, oil mixing, dissolved gasses, or degradation. In various example embodiments, an oil sample identified as being contaminated includes one or more contaminants, such as a chemical component or composition (e.g., water, particles, wear metals, fuels, silicon, or coolant), in an amount that exceeds an acceptable threshold value for the particular contaminant. In various example embodiments, the "oil mixing" defect type indicates that the oil sample exhibits high viscosity and no significant change in the acid number, that the oil sample exhibits low viscosity and no significant change in flash point, or that the oil sample exhibits a presence of different additive metals.

In some example embodiments, if an oil sample is determined to have more than one type of defect based on the oil analysis result, the main reason behind the defects is identified and the dominant defect is selected. For example, if the oil sample is determined to have a high water level, a high acid number, and a high Membrane Patch Colorimetry (MPC) value, two defects are present: contamination and normal degradation. Because the normal degradation happens because of the presence of water (i.e., contamination), a recommendation pertaining to water is provided. The ML model captures this particular pattern as it was trained on historical data, classifies the defect as "contamination," and recommends an appropriate corrective action based on the defect of "contamination."

In some example embodiments, the "dissolved gasses" defect type indicates that the oil sample exhibits low viscosity and a low flash point. In certain example embodiments, the "degradation" defect type indicates that the oil sample exhibits (1) a high Total Acid Number (TAN) result with or without high viscosity, and no significant change in additive metals, (2) a low Rotating Pressure Vessel Oxidation Test (RPVOT) result, (3) a high ultra centrifuge (UC) result, (4) a high MPC result, (5) a low viscosity, and low Viscosity Index (VI) for Viscosity Modifiers (VM) fortified lube oil, or (6) a low Total Base Number (TBN) result for engine oil.

At step 312, the one or more hardware processors 224 classify, using a trained second multiclass classification model, the laboratory analysis results of the oil sample according to the gradient boosting algorithm and the predicted defect type. At step 314, the one or more hardware processors 224 output, using the trained second multiclass classification model, a predicted corrective action pertaining to the equipment based on the predicted defect type for the defect in equipment.

In some example embodiments, the output module 228 generates, at step 316, a workorder based on the predicted corrective action. At step 318, the output module 228 displays the workorder in a user interface of a client device.

Examples of corrective actions are draining the oil in the item of equipment and refilling the item of equipment with fresh oil, checking the integrity of one or more system components and taking corrective action for high wear metals, performing partial replacement to condition the oil, stopping water ingression, removing water by using an adequate filtration system, stopping particle ingression, removing particles by using an adequate filtration system to remove particles, using a varnish removal filter to remove varnish from the lube oil, and degassing the lube oil to remove low-end hydrocarbon from the lube oil.

In some example embodiments, the one or more hardware processors 224 cause performance of the correction action. The one or more hardware processors 224 may cause an adjustment to or an improvement in the step of the item of equipment 220. For example, the one or more hardware processors 224 generate equipment input data 210 based on the identified defect, and transmits an instruction including a reference to the equipment input data 210 to the item of equipment 220 associated with the defect. The execution of the instruction including the reference to the equipment input data 210, by the item of equipment 220, may result in the elimination or the minimization of the identified defect.

In certain example embodiments, the performing of the corrective action includes transmitting a recommendation pertaining to correcting the defect.

In various example embodiments, the laboratory analysis results of the oil sample taken from the equipment include data descriptive of a plurality of parameters of the oil sample. The one or more hardware processors 224 generate a vector including a plurality of features that correspond to the data descriptive of the plurality of parameters of the oil sample. The vector is a digital representation of the results of analysis of a particular oil sample. Examples of features are "Aluminum," "Antimony," "Appear," "Barium," "Boron," "Base Sediment & Water," "Cadmium," "Calcium," "Chromium," "Color," "Copper," "FERL," "FERS," "Filter," "Flash Point," "Foam," "Fuel Dilution," "Iron," "Lead," "Magnesium," "Moisture," "Molybdenum," "Nickel," "pH," "Phosphorous," "Rotating Pressure Vessel Oxidation," "Silicon," "Silver," "Sodium," "Solids," "Total Acid Number," "Total Base Number," "Tin," "Titanium," "Viscosity at 100 degrees Celsius (C)," "Viscosity at 40 degrees C.," "Water," "Zinc," "Oil Type," "Oil Sump Capacity," and "Equipment Type."

According to an example, the lack of a particular parameter (e.g., Aluminum) in the oil sample is indicated, in the vector, with a value of "0" for the feature that corresponds to the particular parameter in the vector. According to another example, the presence of a particular parameter (e.g., Phosphorus) in the oil sample is indicated, in the vector, with a value that indicates an amount of the component (e.g., "80") for the feature that corresponds to the particular parameter in the vector.

The one or more hardware processors 224 associate the vector with a first label that indicates a classification of the oil sample as "good" or "defective" based on the output by the trained binary classification model. The one or more hardware processors 224 associate the vector with a second label that indicates the predicted defect type based on the output by the first trained multiclass classification model. The one or more hardware processors 224 associate the vector with a third label that indicates the corrective action based on the output by the second trained multiclass classification model. The vector representation of the parameters of the oil sample is utilized by the ML models to diagnose the defect associated with the oil sample and predict an appropriate corrective action for the defect. Further details with respect to the operations of the method 300 are described below with respect to FIG. 4.

As shown in FIG. 4, step 402 may be performed before step 302, in which the access module 226 accesses laboratory analysis results of the oil sample from the data repository.

At step 402, the data cleaning module 230 verifies that the laboratory analysis results of the oil sample are complete. At step 402, the data cleaning module 230 identifies the laboratory analysis results of the oil sample as ready for consideration by the binary classification model.

In some example embodiments, only completed and closed records are considered by the ML models. To be a complete and closed record that may be included in a dataset, a record should be labeled and include required features. This allows the ML models to make classification decisions based on adequate information. Records without labels or with missing information may not be part of the dataset used for training the models.

For example, laboratory analysis records that do not include oil type information are not considered by the ML models. In certain example embodiments, the laboratory analysis records that indicate outliers undergo further review (e.g., human review) to determine whether the laboratory analysis records that indicate outliers were misclassified (e.g., a sample classified as defective may actually be a good sample).

In various example embodiments, the results of an oil sample test in conjunction with equipment and oil information is provided as input to the ML models in a specific order or randomly. The example Table 1 below illustrates the features of a defective sample, and how it is classified.

For example, as described at step 302 of FIG. 3, the access module 226 accesses laboratory analysis results of an oil sample (e.g., the input shown in Table 1 below) from a data repository. At step 304, the one or more hardware processors 224 classify, using the trained binary classification model, the laboratory analysis results (e.g., the input shown in Table 1 below) of the oil sample according to a gradient boosting algorithm. At step 306, the one or more hardware processors 224 output, using the trained binary classification model, a classification indicator of "good" or "defective" (e.g., Result of Model 1 Good/Defective: "Defective") for the laboratory analysis results of the oil sample. At step 308, the one or more hardware processors 224 classify, using a trained first multiclass classification model, the laboratory analysis results of the oil sample (e.g., the input shown in Table 1 below) according to the gradient boosting algorithm if the laboratory analysis results are classified as "defective." At step 310, the one or more hardware processors 224 output, using the trained first multiclass classification model, a predicted defect type (e.g., Result of Model 2 Defect Type: "Oil Mixing") for the defect in equipment. At step 312, the one or more hardware processors 224 classify, using a trained second multiclass classification model, the laboratory analysis results (e.g., the input shown in Table 1 below) of the oil sample according to the gradient boosting algorithm and the predicted defect type. At step 314, the one or more hardware processors 224 output, using the trained second multiclass classification model, a predicted corrective action (e.g., Result of Model 3 Corrective Action: "Replace the oil with fresh oil. Adopt color coding to prevent oil mixing") pertaining to the equipment based on the predicted defect type for the defect in equipment.

TABLE 1

| Features and classification of a particular defective sample. | |
|---|---|
| Input | |
| Oil Analysis Lab Result | |
| Aluminum | 0 |
| Antimony | 0 |
| Appear | 1.1 |
| Barium | 0 |
| Boron | 0 |
| Base Sediment & Water | |
| Cadmium | 0 |
| Calcium | 0 |
| Chromium | 0 |
| Color | 2 |
| Copper | 0 |
| Ferl | 1.2 |
| Fers | 1.4 |
| Filter | |
| Flash | 200 |
| Foam | |
| Fuel Dilution | |
| Iron | 0 |
| Lead | 0 |
| Magnesium | 0 |

TABLE 1-continued

| Features and classification of a particular defective sample. | |
|---|---|
| Moisture | 50 |
| Molybdenum | 0 |
| Nickel | 0 |
| PH | 6.1 |
| Phosphorous | 80 |
| Rotating Pressure Vessel Oxidation | 300 |
| Silicon | 0 |
| Silver | 0 |
| Sodium | 0 |
| Solids (UC) | 2 |
| Total Acid Number | 0.14 |
| Total Base Number | |
| Tin | 0 |
| Titanium | 0 |
| Viscosity at 100 degrees C. | |
| Viscosity at 40 degrees C. | 47.5 |
| Zinc | 70 |
| Oil Type | Turbine Oil 46 |
| Equipment Info | |
| Oil Sump Capacity | 300 |
| Equipment Type | Pump |
| Output | |
| Result of Model 1 Good/Defective | Defective |
| Result of Model 2 Defect Type | Oil Mixing |
| Result of Model 3 Corrective Action | Replace the oil with fresh oil. Adopt color coding to prevent oil mixing. |

Figure 5:
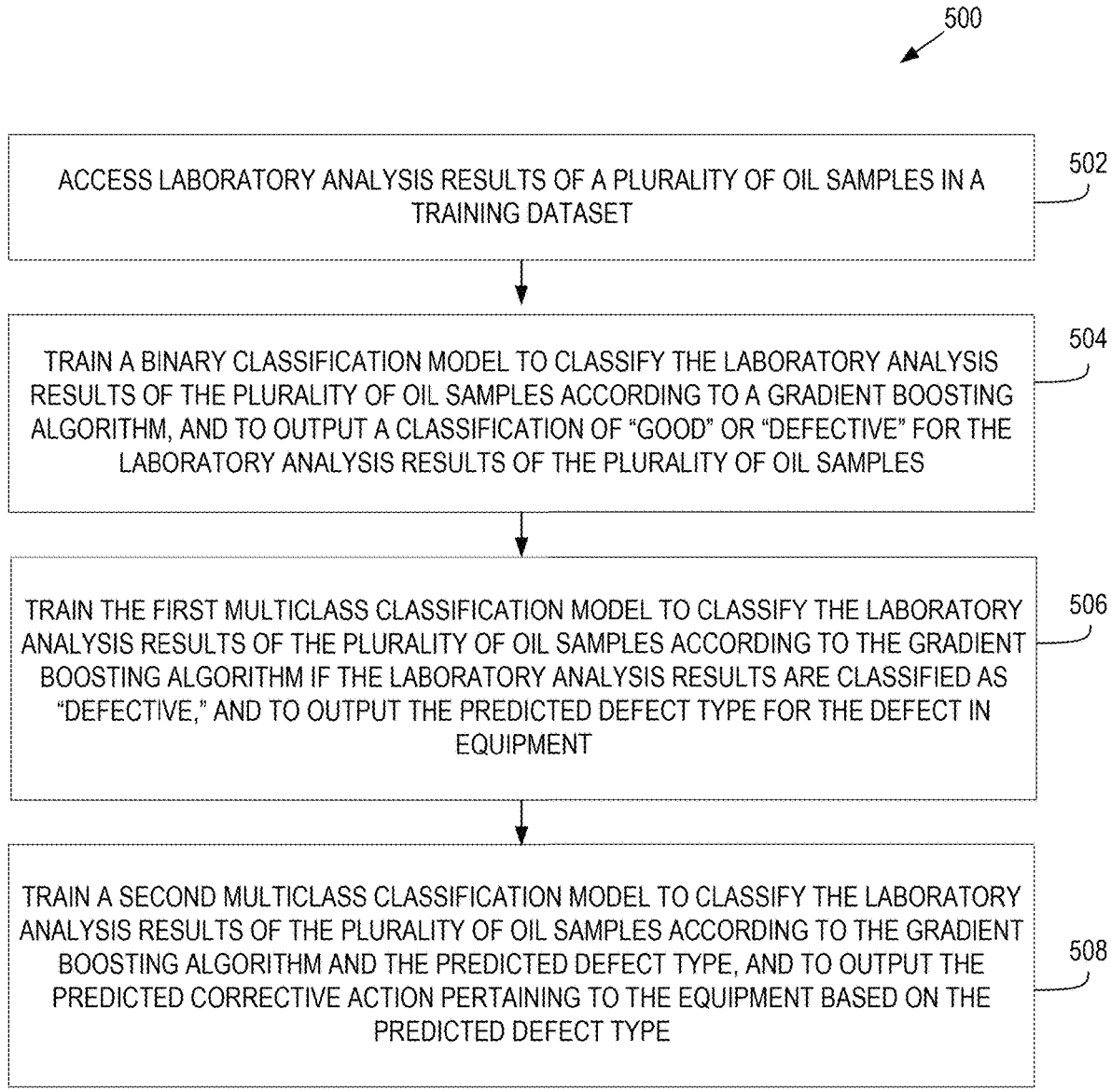
FIGS. 5 and 6 are flowcharts illustrating operations of the diagnostic and correction system in performing a method for training a plurality of classification models to automatically detect a defect in equipment, according to one or more example embodiments.
Figure 6:
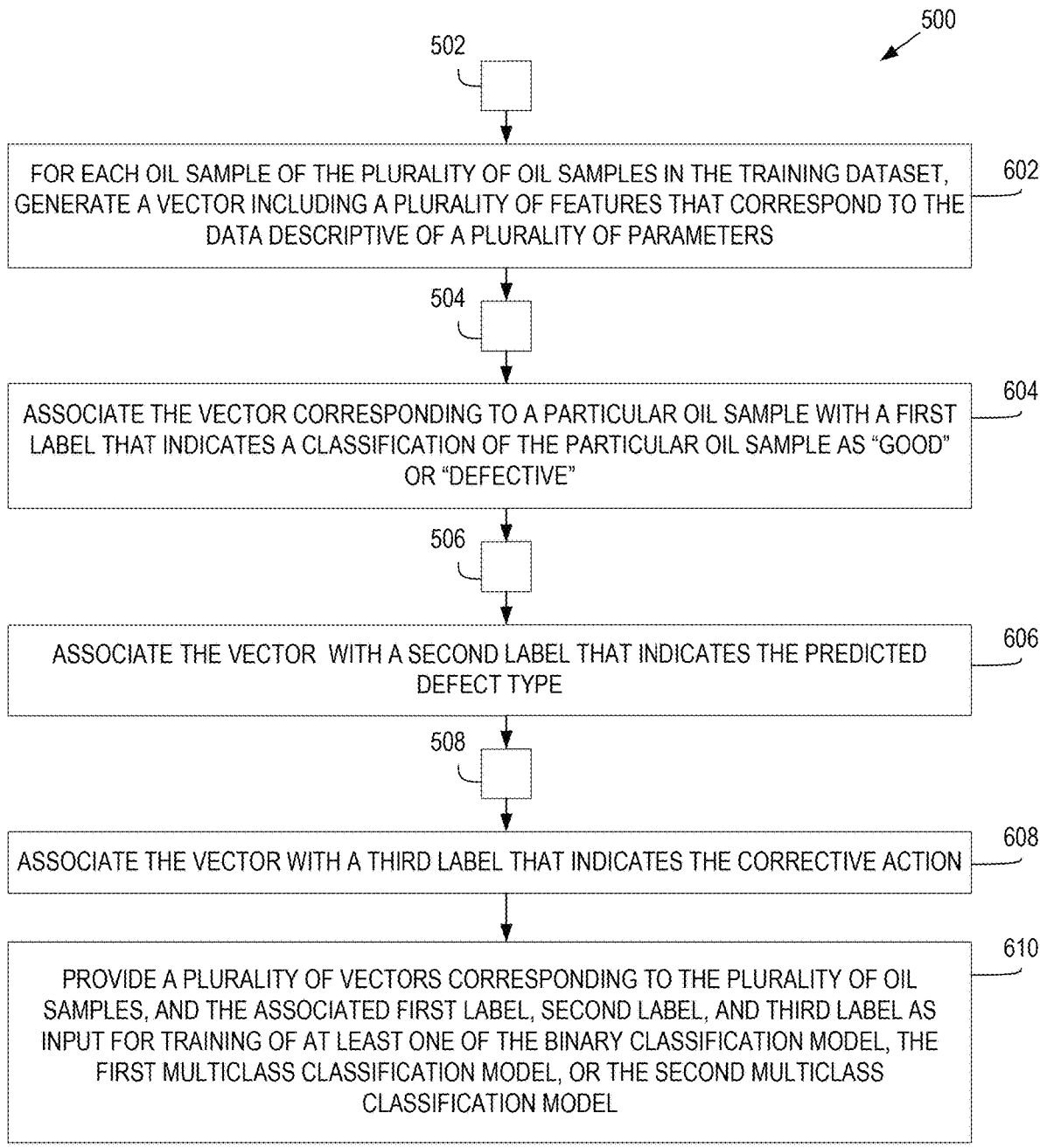

FIGS. 5 and 6 are flowcharts illustrating operations of the diagnostic and correction system in performing a method 500 for training a plurality of classification models to automatically detect a defect in equipment, according to one or more example embodiments. Operations of the method 500 may be performed using the components described above with respect to FIG. 2. One or more blocks in FIGS. 5 and 6 may be performed by a computing system such as that shown and described below in FIGS. 7A and 7B. While the various blocks in FIGS. 5 and 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

At step 502, the access module 226 accesses laboratory analysis results of a plurality of oil samples in a training dataset. The plurality of oil samples may be taken from a variety of operational equipment. The laboratory analysis results of the plurality of oil samples are accessed for use in the training of machine learning models.

In some example embodiments, the data cleaning module 230 verifies that the laboratory analysis results of the plurality of oil samples in the training dataset are complete. The data cleaning module 230 selects the laboratory analysis results of the plurality of oil samples in the training dataset that are verified as complete for consideration by the binary classification model.

At step 504, the one or more hardware processors 224 (e.g., a second processor of a second machine) train a binary classification model to classify the laboratory analysis results of oil samples in the training dataset according to a gradient boosting algorithm, and to output a classification of "good" or "defective" for the laboratory analysis results of the oil samples in the training dataset. For example, the one or more hardware processors 224, based on the parameters included in the laboratory analysis results of a first oil sample in the training dataset, classify the laboratory analysis results of the first oil sample in the training dataset into a first class (e.g., a class identified as "good samples"). The one or more hardware processors 224, based on the parameters included in the laboratory analysis results of a second oil sample in the training dataset, classify the laboratory analysis results of the second oil sample in the training dataset into a second class (e.g., a class identified as "defective samples").

In various example embodiments, the one or more hardware processors 224 oversample the laboratory analysis results of the plurality of oil samples in the training dataset using a Synthetic Minority Oversampling Technique (SMOTE) and a first support vector machine (SVM) algorithm to balance a "good" class and a "defective" class with respect to a distribution of the laboratory analysis results of the plurality of oil samples in the training dataset. The binary classification model is trained on a first percentage (e.g., eighty percent) of the oversampled laboratory analysis results. A second percentage (e.g., the remaining twenty percent) of the oversampled laboratory analysis results are used to test the prediction performance of the binary classification model.

In some example embodiments, the one or more hardware processors 224 associate the output of the binary classification model with a particular laboratory analysis record of a particular oil sample in the training dataset. The associating may include attaching a first label that indicates the classification of the laboratory analysis record into a "good" class (e.g., the value "0") or "defective" class (e.g., the value "1").

At step 506, the one or more hardware processors 224 train the first multiclass classification model to classify the laboratory analysis results of the oil samples in the training dataset according to the gradient boosting algorithm if the laboratory analysis results are classified as "defective," and to output a predicted defect type for the defect in equipment.

In various example embodiments, the one or more hardware processors 224 oversample the laboratory analysis results of the plurality of oil samples in the training dataset that are classified as "defective." The oversampling is performed using SMOTE and a second SVM algorithm to balance a plurality of defect-type classes with respect to a distribution of the laboratory analysis results of the plurality of oil samples in the training dataset that are classified as "defective." The first multiclass classification model is trained on a first percentage of the oversampled laboratory analysis results classified as "defective." A second percentage of the oversampled laboratory analysis results classified as "defective" are used to test the prediction performance of the first multiclass classification model.

In some example embodiments, the one or more hardware processors 224 associate the output of the first multiclass classification model with a particular laboratory analysis record of a particular oil sample in the training dataset. The associating may include attaching a second label that indicates the classification of a defective laboratory analysis record into a particular defect-type class.

At step 508, the one or more hardware processors 224 train a second multiclass classification model to classify the laboratory analysis results of the oil samples in the training dataset according to the gradient boosting algorithm and the predicted defect type, and to output a predicted corrective action pertaining to the equipment based on the predicted defect type for the defect in equipment. In some example embodiments, the training of the second multiclass classification model to output the predicted corrective action is further based on historical expert decisions.

In various example embodiments, the one or more hardware processors 224 generate, for each defect type, a dataset from the laboratory analysis results of the plurality of oil samples in the training dataset that are classified as "defective." The one or more hardware processors 224 oversample, for each defect type, the dataset using SMOTE and a third SVM algorithm. The second multiclass classification model is trained on a first percentage of the oversampled dataset. A second percentage of the oversampled dataset is used to test the prediction performance of the second multiclass classification model.

In some example embodiments, the one or more hardware processors 224 associate the output of the second multiclass classification model with a particular laboratory analysis record of a particular oil sample in the training dataset. The associating may include attaching a third label that indicates the predicted corrective action determined for the particular oil sample in the training dataset. Further details with respect to the operations of the method 500 are described below with respect to FIG. 6.

As shown in FIG. 6, the method 500 may include one or more of operations 602, 604, 606, 608, and 610, according to some example embodiments. In some example embodiments, the laboratory analysis results of the plurality of oil samples in the training dataset include data descriptive of a plurality of parameters (e.g., aspects, attributes, or characteristics) of the plurality of oil samples in the training dataset. A parameter may be a chemical component or composition present in an oil sample, or a physical characteristic of the oil sample. Examples of parameters are water, particles, wear metals, fuels, silicon, coolant, viscosity level, additive metals, and flash point level.

Step 602 may be performed after step 502, in which the access module 226 accesses laboratory analysis results of a plurality of oil samples in a training dataset. At step 602, the one or more hardware processors 224 (e.g., the second processor of the second machine) generate, for each oil sample of the plurality of oil samples in the training dataset, a vector including a plurality of features that correspond to the data descriptive of the plurality of parameters.

Step 604 may be performed after step 504, in which the one or more hardware processors 224 train a binary classification model to classify the laboratory analysis results of a plurality of oil samples in a training dataset according to a gradient boosting algorithm, and to output a classification of "good" or "defective" for the laboratory analysis results of the oil samples in the training dataset. At step 604, the one or more hardware processors 224 associate the vector corresponding to a particular oil sample with a first label that indicates a classification of the particular oil sample as "good" or "defective" based on the output by the binary classification model.

Step 606 may be performed after step 506, in which the one or more hardware processors 224 train the first multiclass classification model to classify the laboratory analysis results of the oil samples in the training dataset according to the gradient boosting algorithm if the laboratory analysis results are classified as "defective," and to output a predicted defect type for the defect in equipment. At step 606, the one or more hardware processors 224 associate the vector corresponding to the particular oil sample with a second label that indicates the predicted defect type based on the output by the first multiclass classification model.

Step 608 may be performed after step 508, in which the one or more hardware processors 224 train a second multiclass classification model to classify the laboratory analysis results of the oil samples in the training dataset according to the gradient boosting algorithm and the predicted defect type, and to output a predicted corrective action pertaining to the equipment based on the predicted defect type for the defect in equipment. At step 608, the one or more hardware processors 224 associate the vector corresponding to the particular oil sample with a third label that indicates the corrective action based on the output by the second multiclass classification model.

At step 610, the one or more hardware processors 224 provide a plurality of vectors corresponding to the plurality of oil samples in the training dataset, and the associated first label, second label, and third label as input for the training of at least one of the binary classification model, the first multiclass classification model, or the second multiclass classification model.

Figure 7A:
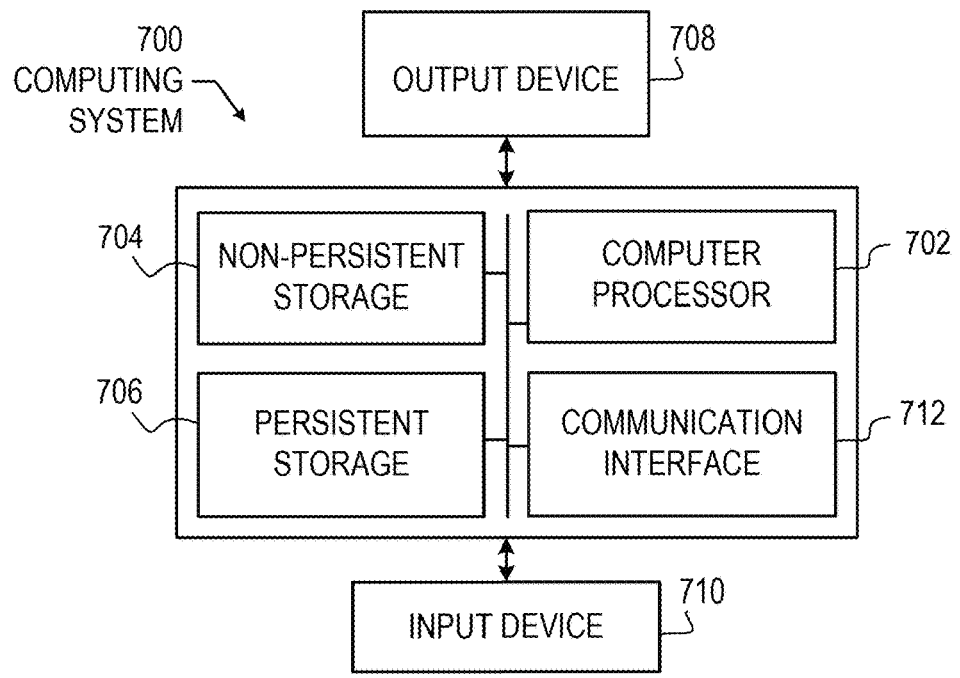
FIGS. 7A and 7B illustrate a computing system, according to one or more example embodiments.

Example embodiments may be implemented on a computing system. Any combination of mobile, desktop, server, router, switch, embedded device, or other types of hardware may be used. For example, as shown in FIG. 7A, the computing system 700 may include one or more computer processors 702, non-persistent storage 704 (e.g., volatile memory, such as random access memory (RAM) or cache memory), persistent storage 706 (e.g., a hard disk, an optical drive such as a compact disk (CD) drive or digital versatile disk (DVD) drive, or a flash memory), a communication interface 712 (e.g., Bluetooth interface, infrared interface, network interface, or optical interface), and numerous other elements and functionalities.

The computer processor(s) 702 may be an integrated circuit for processing instructions. For example, the computer processor(s) 702 may be one or more cores or microcores of a processor. The computing system 700 may also include one or more input devices 710, such as a touchscreen, keyboard, mouse, microphone, touchpad, or electronic pen.

The communication interface 712 may include an integrated circuit for connecting the computing system 700 to a network (not shown) (e.g., a local area network (LAN), a wide area network (WAN), such as the Internet, mobile network, or any other type of network) or to another device, such as another computing device.

Further, the computing system 700 may include one or more output devices 708, such as a screen (e.g., a liquid crystal display (LCD), a plasma display, touchscreen, cathode ray tube (CRT) monitor, or projector), a printer, external storage, or any other output device. One or more of the output devices may be the same or different from the input device(s). The input and output device(s) may be locally or remotely connected to the computer processor(s) 702, non-persistent storage 704, and persistent storage 706. Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s) is configured to perform one or more embodiments of the disclosure.

Figure 7B:
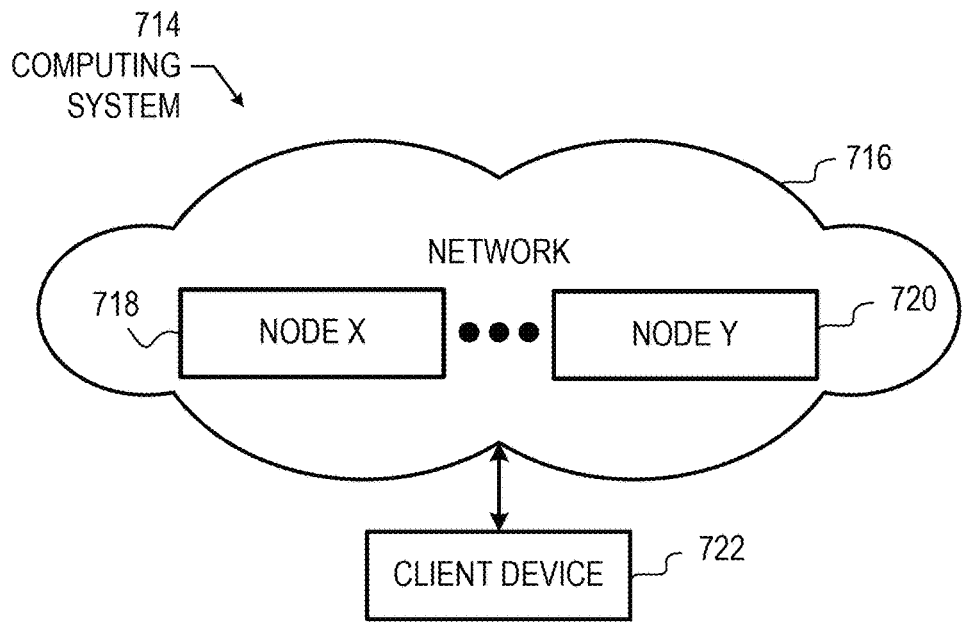

The computing system 700 in FIG. 7A may be connected to or be a part of a network. For example, as shown in FIG. 7B, the network 716 may include multiple nodes (e.g., node X 718 or node Y 720). Each node may correspond to a computing system, such as the computing system shown in FIG. 7A, or a group of nodes combined may correspond to the computing system shown in FIG. 7A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system 700 may be located at a remote location and connected to the other elements over a network.

Although not shown in FIG. 7B, the node may correspond to a blade in a server chassis that is connected to other nodes via a backplane. By way of another example, the node may correspond to a server in a data center. By way of another example, the node may correspond to a computer processor or micro-core of a computer processor with shared memory or resources.

The nodes (e.g., node X 718 or node Y 720) in the network 716 may be configured to provide services for a client device 722. For example, the nodes may be part of a cloud computing system. The nodes may include functionality to receive requests from the client device 722 and transmit responses to the client device 722. The client device 722 may be a computing system, such as the computing system shown in FIG. 7A. Further, the client device 722 may include or perform all or a portion of one or more embodiments of the disclosure.

The computing system or group of computing systems described in FIGS. 7A and 7B may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided in subsequent paragraphs.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the selection by the user.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the selection by the user. Further to the above example, the data received from the server after selecting the URL link may provide a web page in Hyper Text Markup Language (HTML) that may be rendered by the web client and displayed on the user device.

The computing system in FIG. 7A may implement or be connected to a data repository. For example, one type of data repository is a database. A database is a collection of information configured for ease of data retrieval, modification, re-organization, and deletion. Database management system (DBMS) is a software application that provides an interface for users to define, create, query, update, or administer databases.

The user, or software application, may submit a statement or query into the DBMS.

Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g., join, full join, count, or average), sort (e.g., ascending or descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 7A may include functionality to present raw or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, for example, data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, for example, by obtaining data from a data attribute within the data object that identifies the data object type. Then, the GUI may determine any rules designated for displaying that data object type, for example, rules specified by a software framework for a data object class or according to any local parameters defined by the GUI for presenting that data object type. Finally, the GUI may obtain data values from the particular data object and render a visual representation of the data values within a display device according to the designated rules for that data object type.

The previous description of functions presents only a few examples of functions performed by the computing system of FIG. 7A and the nodes or client device in FIG. 7B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed. Accordingly, the scope of the disclosure should be limited only by the attached claims.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A system for automatic detection of a defect in equipment, the system comprising:
   one or more hardware processors;

an access module executed by the one or more hardware processors and configured to access laboratory analysis results of an oil sample taken from the equipment;
a binary classification model trained by the one or more hardware processors to:
 classify the laboratory analysis results of the oil sample according to a gradient boosting algorithm, and
 output a classification indicator of "good" or "defective" for the laboratory analysis results of the oil sample;
a data cleaning module configured to:
 verify that the laboratory analysis results of the oil sample are complete by ensuring that the laboratory analysis results are labeled and closed, and
 identify, with a tag or mark, the laboratory analysis results of the oil sample as ready for consideration by the binary classification model;
a first multiclass classification model trained by the one or more hardware processors to:
 classify the laboratory analysis results of the oil sample according to the gradient boosting algorithm if the laboratory analysis results are classified as "defective" by the binary classification model, and
 output a predicted defect type for the defect in equipment; and
a second multiclass classification model trained by the one or more hardware processors to:
 classify the laboratory analysis results of the oil sample according to the gradient boosting algorithm and the predicted defect type, and
 output a predicted corrective action pertaining to the equipment based on the predicted defect type for the defect in equipment output by the first multiclass classification model,
wherein the access module comprises software instructions forming computer readable code;
wherein the binary classification model comprises a first Machine Learning (ML) model, the first multiclass classification model comprises a second ML model, and the second multiclass classification model comprises a third ML model;
wherein the one or more hardware processors transmit input data to the equipment that modifies an operation of the equipment and automatically causes performance of the predicted corrective action;
wherein the equipment comprises an internal combustion engine, a pump, a gearbox, a pipe connection, derrick components, drawworks, or wire ropes, and
wherein the predicted corrective action comprises refilling the equipment with fresh oil, conditioning oil in the equipment, stopping water or particle ingression into the oil in the equipment, removing water or particles from the equipment with a filtration system, removing varnish from the oil in the equipment, or degassing the oil in the equipment.

2. The system of claim 1, wherein the access module is further configured to access laboratory analysis results of a plurality of oil samples in a training dataset, and
 wherein the one or more hardware processors are configured to:
  train the binary classification model to:
   classify the laboratory analysis results of the plurality of oil samples in the training dataset according to the gradient boosting algorithm, and
   output a classification of "good" or "defective" for the laboratory analysis results of the plurality of oil samples in the training dataset;
  train the first multiclass classification model to:
   classify the laboratory analysis results of the plurality of oil samples in the training dataset according to the gradient boosting algorithm if the laboratory analysis results are classified as "defective," and
   output the predicted defect type for the defect in equipment; and
  train a second multiclass classification model to:
   classify the laboratory analysis results of the plurality of oil samples in the training dataset according to the gradient boosting algorithm and the predicted defect type, and
   output the predicted corrective action pertaining to the equipment based on the predicted defect type for the defect in equipment.

3. The system of claim 2, wherein the one or more hardware processors are further configured to oversample the laboratory analysis results of the plurality of oil samples in the training dataset using a Synthetic Minority Oversampling Technique (SMOTE) and a first support vector machine (SVM) algorithm to balance a "good" class and a "defective" class with respect to a distribution of the laboratory analysis results of the plurality of oil samples in the training dataset,
 wherein the binary classification model is trained on a first percentage of the oversampled laboratory analysis results, and
 wherein a second percentage of the oversampled laboratory analysis results are used to test the prediction performance of the binary classification model.

4. The system of claim 2, wherein the one or more hardware processors are further configured to oversample the laboratory analysis results of the plurality of oil samples in the training dataset that are classified as "defective," the oversampling being performed using a Synthetic Minority Oversampling Technique (SMOTE) and a second support vector machine (SVM) algorithm to balance a plurality of defect-type classes with respect to a distribution of the laboratory analysis results of the plurality of oil samples in the training dataset that are classified as "defective,"
 wherein the first multiclass classification model is trained on a first percentage of the oversampled laboratory analysis results classified as "defective," and
 wherein a second percentage of the oversampled laboratory analysis results classified as "defective" are used to test the prediction performance of the first multiclass classification model.

5. The system of claim 2, wherein the one or more hardware processors are further configured to:
 for each defect type, generate a dataset from the laboratory analysis results of the plurality of oil samples in the training dataset that are classified as "defective," and
 for each defect type, oversample the dataset using a Synthetic Minority Oversampling Technique (SMOTE) and a third support vector machine (SVM) algorithm,
 wherein the second multiclass classification model is trained on a first percentage of the oversampled dataset, and
 wherein a second percentage of the oversampled dataset is used to test the prediction performance of the second multiclass classification model.

6. The system of claim 2, wherein the laboratory analysis results of the plurality of oil samples in the training dataset include data descriptive of a plurality of parameters of the plurality of oil samples in the training dataset, and
 wherein the one or more hardware processors are further configured to:

for each oil sample of the plurality of oil samples in the training dataset, generate a vector including a plurality of features that correspond to the data descriptive of the plurality of parameters;

associate the vector corresponding to a particular oil sample with a first label that indicates a classification of the particular oil sample as "good" or "defective" based on the output by the binary classification model;

associate the vector corresponding to the particular oil sample with a second label that indicates the predicted defect type based on the output by the first multiclass classification model;

associate the vector corresponding to the particular oil sample with a third label that indicates the corrective action based on the output by the second multiclass classification model; and provide a plurality of vectors corresponding to the plurality of oil samples in the training dataset, and the associated first label, second label, and third label as input for the training of at least one of the binary classification model, the first multiclass classification model, or the second multiclass classification model.

7. The system of claim 2, wherein the training of the second multiclass classification model to output the predicted corrective action is further based on historical expert decisions.

8. The system of claim 2, wherein the data cleaning module is further configured to:
verify that the laboratory analysis results of the plurality of oil samples in the training dataset are complete; and
select the laboratory analysis results of the plurality of oil samples in the training dataset that are verified as complete for consideration by the binary classification model.

9. The system of claim 1, wherein the laboratory analysis results of the oil sample taken from the equipment include data descriptive of a plurality of parameters of the oil sample, and
wherein the one or more hardware processors are configured to:
generate a vector including a plurality of features that correspond to the data descriptive of the plurality of parameters of the oil sample;
associate the vector with a first label that indicates a classification of the oil sample as "good" or "defective" based on the output by the binary classification model;
associate the vector with a second label that indicates the predicted defect type based on the output by the first multiclass classification model; and
associate the vector with a third label that indicates the corrective action based on the output by the second multiclass classification model.

10. The system of claim 1, further comprising:
an output module configured to:
generate a workorder based on the predicted corrective action, and
display the workorder in a user interface of a client device.

11. A method for automatic detection of a defect in equipment, the method comprising:
accessing, by an access module executed by one or more hardware processors, laboratory analysis results of an oil sample taken from the equipment;

verifying, with a data cleaning module, that the laboratory analysis results of the oil sample are complete by ensuring that the laboratory analysis results are labeled and closed;

identifying, with the data cleaning module and using a tag or mark, the laboratory analysis results of the oil sample as ready for consideration by a trained binary classification model;

classifying, by the one or more hardware processors using the trained binary classification model, the laboratory analysis results of the oil sample according to a gradient boosting algorithm;

outputting, by the one or more hardware processors using the trained binary classification model, a classification indicator of "good" or "defective" for the laboratory analysis results of the oil sample;

classifying, by the one or more hardware processors using a trained first multiclass classification model, the laboratory analysis results of the oil sample according to the gradient boosting algorithm if the laboratory analysis results are classified as "defective;"

outputting, by the one or more hardware processors using the trained first multiclass classification model, a predicted defect type for the defect in equipment;

classifying, by the one or more hardware processors using a trained second multiclass classification model, the laboratory analysis results of the oil sample according to the gradient boosting algorithm and the predicted defect type;

outputting, by the one or more hardware processors using the trained second multiclass classification model, a predicted corrective action pertaining to the equipment based on the predicted defect type for the defect in equipment, and transmitting, with the one or more hardware processors, input data to the equipment that modifies an operation of the equipment and automatically causes performance of the predicted corrective action, wherein the access module comprises software instructions forming computer readable code;

wherein the binary classification model comprises a first Machine Learning (ML) model, the first multiclass classification model comprises a second ML model, and the second multiclass classification model comprises a third ML model;

wherein the equipment comprises an internal combustion engine, a pump, a gearbox, a pipe connection, derrick components, drawworks, or wire ropes, and wherein the predicted corrective action comprises refilling the equipment with fresh oil, conditioning oil in the equipment, stopping water or particle ingression into the oil in the equipment, removing water or particles from the equipment with a filtration system, removing varnish from the oil in the equipment, or degassing the oil in the equipment.

12. The method of claim 11, wherein the laboratory analysis results of the oil sample taken from the equipment include data descriptive of a plurality of parameters of the oil sample, and
wherein the method further comprises:
generating, by the one or more hardware processors, a vector including a plurality of features that correspond to the data descriptive of the plurality of parameters of the oil sample;
associating, by the one or more hardware processors, the vector with a first label that indicates a classification of the oil sample as "good" or "defective" based on the output by the binary classification model;

associating, by the one or more hardware processors, the vector with a second label that indicates the predicted defect type based on the output by the first multiclass classification model; and associating, by the one or more hardware processors, the vector with a third label that indicates the corrective action based on the output by the second multiclass classification model.

13. A method for training a plurality of classification models to automatically detect a defect in equipment, the method comprising:

accessing laboratory analysis results of a plurality of oil samples in a training dataset;

training, by one or more hardware processors, a binary classification model to:
classify the laboratory analysis results of oil samples in the training dataset according to a gradient boosting algorithm, and
output a classification of "good" or "defective" for the laboratory analysis results of the oil samples in the training dataset;

verifying, with a data cleaning module, that the laboratory analysis results of the oil sample are complete by ensuring that the laboratory analysis results are labeled and closed;

identifying, with the data cleaning module and using a tag or mark, the laboratory analysis results of the oil sample as ready for consideration by a trained binary classification model;

training, by the one or more hardware processors, a first multiclass classification model to:
classify the laboratory analysis results of the oil samples in the training dataset according to the gradient boosting algorithm if the laboratory analysis results are classified as "defective," and
output the predicted defect type for the defect in equipment; and training, by the one or more hardware processors, a second multiclass classification model to:
classify the laboratory analysis results of the oil samples in the training dataset according to the gradient boosting algorithm and the predicted defect type;

output a predicted corrective action pertaining to the equipment based on the predicted defect type for the defect in equipment, and transmitting, with the one or more hardware processors, input data to the equipment that modifies an operation of the equipment and automatically causes performance of the predicted corrective action, wherein accessing of the laboratory analysis results of the plurality of oil samples is performed with software instructions forming computer readable code;

wherein the binary classification model comprises a first Machine Learning (ML) model, the first multiclass classification model comprises a second ML model, and the second multiclass classification model comprises a third ML model;

wherein the equipment comprises an internal combustion engine, a pump, a gearbox, a pipe connection, derrick components, drawworks, or wire ropes, and wherein the predicted corrective action comprises refilling the equipment with fresh oil, conditioning oil in the equipment, stopping water or particle ingression into the oil in the equipment, removing water or particles from the equipment with a filtration system, removing varnish from the oil in the equipment, or degassing the oil in the equipment.

14. The method of claim 13, further comprising:
oversampling the laboratory analysis results of the plurality of oil samples in the training dataset using a Synthetic Minority Oversampling Technique (SMOTE) and a first support vector machine (SVM) algorithm to balance a "good" class and a "defective" class with respect to a distribution of the laboratory analysis results of the plurality of oil samples in the training dataset, wherein the binary classification model is trained on a first percentage of the oversampled laboratory analysis results, and wherein a second percentage of the oversampled laboratory analysis results are used to test the prediction performance of the binary classification model.

15. The method of claim 13, further comprising:
oversampling the laboratory analysis results of the plurality of oil samples in the training dataset that are classified as "defective," the oversampling being performed using a Synthetic Minority Oversampling Technique (SMOTE) and a second support vector machine (SVM) algorithm to balance a plurality of defect-type classes with respect to a distribution of the laboratory analysis results of the plurality of oil samples in the training dataset that are classified as "defective,"

wherein the first multiclass classification model is trained on a first percentage of the oversampled laboratory analysis results classified as "defective," and wherein a second percentage of the oversampled laboratory analysis results classified as "defective" are used to test the prediction performance of the first multiclass classification model.

16. The method of claim 13, further comprising:
for each defect type, generating a dataset from the laboratory analysis results of the plurality of oil samples in the training dataset that are classified as "defective;" and for each defect type, oversampling the dataset using a Synthetic Minority Oversampling Technique (SMOTE) and a third support vector machine (SVM) algorithm, wherein the second multiclass classification model is trained on a first percentage of the oversampled dataset, and wherein a second percentage of the oversampled dataset is used to test the prediction performance of the second multiclass classification model.

17. The method of claim 13, wherein the laboratory analysis results of the plurality of oil samples in the training dataset include data descriptive of a plurality of parameters of the plurality of oil samples in the training dataset, and wherein the method further comprises:
for each oil sample of the plurality of oil samples in the training dataset, generating a vector including a plurality of features that correspond to the data descriptive of the plurality of parameters;

associating the vector corresponding to a particular oil sample with a first label that indicates a classification of the particular oil sample as "good" or "defective" based on the output by the binary classification model;

associating the vector corresponding to the particular oil sample with a second label that indicates the predicted defect type based on the output by the first multiclass classification model;

associating the vector corresponding to the particular oil sample with a third label that indicates the corrective action based on the output by the second multiclass classification model; and providing a plurality of vectors corresponding to the plurality of oil samples in the training dataset, and the associated first label, second label, and third label as input for the training of at least one of the binary classification model, the first multiclass classification model, or the second multiclass classification model.

18. The method of claim 13, wherein the training of the second multiclass classification model to output the predicted corrective action is further based on historical expert decisions.

* * * * *